United States Patent [19]

Wittmann et al.

[11] 4,256,482
[45] Mar. 17, 1981

[54] HERBICIDAL COMPOSITION

[75] Inventors: Erwin Wittmann; Alfred Diskus, both of Linz; Engelbert Auer, Leonding, all of Austria

[73] Assignee: Chemie Linz Aktiengesellschaft, Linz, Austria

[21] Appl. No.: 77,762

[22] Filed: Sep. 21, 1979

[30] Foreign Application Priority Data

Sep. 29, 1978 [AT] Austria .................... 7031/78

[51] Int. Cl.³ .................... A01N 43/66; A01N 43/58
[52] U.S. Cl. .................................... 71/92; 71/93
[58] Field of Search .................... 71/92, 93

[56] References Cited

U.S. PATENT DOCUMENTS 3,953,445  10/1976  Fischer ............................ 71/92

FOREIGN PATENT DOCUMENTS 45-38000  12/1970  Japan ............................ 71/93
50-36637   4/1975  Japan ............................ 71/93
1132306   10/1968  United Kingdom ................. 71/93

OTHER PUBLICATIONS

Diskus et al. Proc. 9th British Weed Control Conf. 1976, vol. 2, p. 717.

Primary Examiner—Donald G. Daus
Assistant Examiner—D. B. Springer
Attorney, Agent, or Firm—Wenderoth, Lind & Ponack

[57] ABSTRACT

Herbicidal composition which comprises as active ingredients a phenylpyridazine of the formula

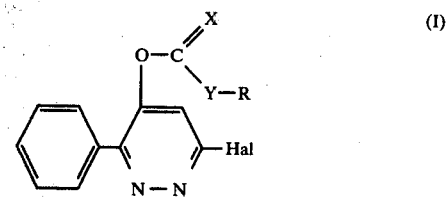

in which Hal is chlorine or bromine, R is alkyl with up to 12 C-atoms and X and Y are oxygen or sulfur, whereby one of X and Y always is sulfur and 2-{[4-chloro-6-(ethylamino)-S-triazin-2-yl]amino}-2-methyl-propionitrile.

This composition is particularly used in combating weeds which are difficult to combat and are found in growing cereal crops.

6 Claims, No Drawings

HERBICIDAL COMPOSITION

The invention relates to a new herbicidal composition which comprises as active ingredients a phenylpyridazine and 2-{[4-chloro-6-(ethylamino)-s-triazin-2-yl]amino}-2-methylpropionitrile, and has a particularly high selective and synergistic action in combating weeds, and to a process for combating weeds, in particular weeds which are difficult to combat and are found in growing cereal crops, as *Anthemis arvensis*, *Stellaria media* and *Galium aparine*.

In U.S. Pat. No. 3,953,445 phenylpyridazines of the formula

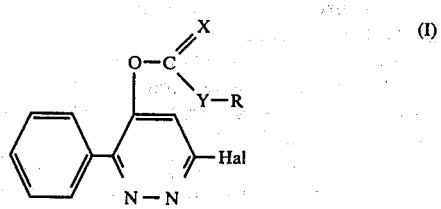

are described, in which Hal is chlorine or bromine, R is a straight-chain alkyl or branched alkyl with up to 12 C atoms or phenyl, X is oxygen or sulfur and Y is a sulfur atom or oxygen, whereby one of X and Y always is sulfur which have herbicidal properties and are distinguished by being well tolerated by many useful plants, including cereal crops.

The compound 0-[3-phenyl-6-chloro-pyridazin-4-yl] S-(n-octyl)-thiocarbonate has proved particularly suitable as an agent for combating weeds in cereal crops and maize crops (Diskus et al., Proc. 9th British Weed Control Conf. 1976, Vol. 2, Page 717).

The phenylpyridazines according to formula I attack a broad spectrum of weeds. However, when used in practice in the open, it was found that some varieties of weeds, such as, for example, *Anthemis arvensis* (corn chamomile) and *Stellaria media* (chickweed) require relatively high dosages of active compound to be combated effectively. This is in particular the case when the weeds are in an advanced stage of development. Thus, at the point of time at which spraying with the herbicide takes place, it is frequently found that *Galium aparine* has already developed side shoots, *Stellaria media* is as a rule about to flower and even *Anthemis arvensis* has usually already developed more than 10 true leaves.

Under these conditions, the dosages necessary to adequately combat the weeds are higher than those in the case of model experiments in a greenhouse.

It is also known, from British Pat. No. 1,132,306, that the compound 2-{[4-chloro-6-(ethylamino)-s-triazin-2-yl]amino}-2-methylpropionitrile ("Cyanazine") can be used as a herbicide in cereal crops by the post emergence method. However, the dosage must be kept relatively low (0.25 to 0.5 kg of active compound/ha), since higher amounts also damage the useful plants. Some varieties of weed, in particular *Galium aparine* (catchweed bedstraw), one of the weeds in cereal crops which are most important from the point of view of economics, are not attacked or are attacked to a completely inadequate extent in these low dosages.

It has now been found that mixtures of active compounds of the phenylpyridazine group of the formula I, in particular the compound 0-[3-phenyl-6-chloro-pyridazin-4-yl]S-(n-octyl) thiocarbonate (Pyridate), and the active compound 2-{[4-chloro-6-(ethylamino)-s-triazin-2-yl]amino}-2-methylpropionitrile ("Cyanazine") have a degree of herbicidal action which is considerably greater than the degree of action which could be expected from the sum of the actions of the two individual components. This effect is a potentiation of the herbicidal properties in the sense of synergism. This synergistic effect in a mixture of the active compounds indicated could in no way be foreseen and must be regarded as distinctly surprising.

The present invention accordingly relates to a herbicidal composition, comprising as active ingredients one or more phenylpyridazines of the formula

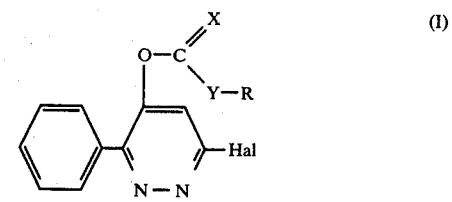

in which Hal is chlorine or bromine, R is a straight-chain alkyl or branched alkyl, both having up to 12 C atoms or phenyl, X is oxygen or sulfur and Y is sulfur or oxygen, whereby one of X and Y always is sulfur, and the compound 2-{[4-chloro-6-(ethylamino)-s-triazin-2-yl]amino}-2-methylpropionitrile.

This increased degree of herbicidal action of this composition, which extends beyond a simple additive effect provides considerably technical advantages. Thus it is possible, on the one hand, to lower considerably the amounts of individual components applied per unit area treated, and on the other hand, the attack on weeds such as, for example, *Anthemis arvensis*, which could not hitherto be adequately combated in the open with either of the two types of active compound, is considerably better than previously.

Amongst the compounds of the formula I, the compounds 0-[3-phenyl-6-chloro-pyridazin-4-yl]S-(n-propyl)thiocarbonate, 0-[3-phenyl-6-chloro-pyridazin-4-yl]S-(n-butyl)thiocarbonate, 0-[3-phenyl-6-bromopyridazin-4-yl]S-(n-butyl)thiocarbonate and 0-[3-phenyl-6-chloro-pyridazin-4-yl]S-(n-dodecyl) thiocarbonate in combination with Cyanazine give very favorable results. The combination of 0-[3-phenyl-6-chloropyridazin-4-yl]S-(n-octyl) thiocarbonate ("Pyridate") and Cyanazine is particularly preferred. The weight ratio of this two compounds is preferably in the range from 1:0,6 to 1:15.

The composition according to the invention can be converted into the customary formulations, such as solutions, emulsuions, dispersions, powders, pastes and granules. These formulations are produced in a known manner, for example by mixing the active compounds with extenders, that is to say liquid solvents and/or solid carriers, if appropriate using surface-active agents, that is to say emulsifying agents and/or wetting agents and dispersing agents. Possible fillers and carriers for the wettable powder formulations, which are particularly suitable, are, in the main: ground minerals, such as kaolins, clays, talcs, chalks and synthetically produced highly disperse silica. Suitable wetting agents and dispersing agents are ionic and non-ionic surface-active agents, such as Na dialkylarylsulfonates, Na alkyl-aryl-sulfonates, Na alkyl-sulfates, Na alkylaryl-sulfates and polyoxyethylene compounds; Na oleylmethyl-tauride, Na salts of phenolsulfonic acid condensation products, Na alkylnaphthalenesulfonate/formaldehyde condensation products and ligninsulfite waste liquor powder.

The composition according to the invention can be formulated as a wettable powder, preferably in accordance with the following recipe:

| | |
|---|---|
| Active compound of the formula I | 12–45% by weight |
| Cyanazine | 3–20% by weight |
| Wetting agents and dispersing agents | 5–15% by weight |
| Inert fillers and carriers to make up to 100% | |

For use, this formulation is suspended in water. It can also contain other known active compounds, such as herbicides, fungicides and growth regulators.

It is possible to use the composition according to the invention as a herbicidal agent in a number of crops, such as, for example, cereal crops or maize crops. It is used by the post-emergence method.

The amounts of the composition according to the invention applied can be varied within a certain range. They depend on the ratio of the active compounds in the composition and on the nature of the weeds. The active compound of the general formula I is usually applied in an amount of 0.25 to 1.5 kg/ha and the active compound Cyanazine is applied in an amount of 0.1 to 0.4 kg/ha.

It is particularly preferably to use the composition according to the invention in cereal crops, the active compound of the formula I being applied in an amount of 0.5 to 1.5 kg/ha and the active compound Cyanazine being applied in an amount of 0.1 to 0.4 kg/ha. If the active compoud 0-[3-phenyl-6-chloro-pyridazin-4-yl]S-(n-octyl)thiocarbonate is used in combination with Cyanazine, it should appropriately be combined so that it is applied in an amount of 0.5 kg/ha with at least 0.3 kg/ha of Cyanazine in order to adequately combat the 3 varieties of weed *Galium aparine, Stellaria media* and *Anthemis arvensis*. When the active compound 0-[3-phenyl-6-chloropyridazin-4-yl]S-(n-octyl)thiocarbonate is applied in an amount of 0.75 kg/ha in combination with 0.3 kg/ha of Cyanazine, a degree of herbicidal action of 100% is achieved in the case of *Galium aparine* and *Stellaria media* and the effect on *Anthemis arvensis* is also already completely satisfactory.

If the active compound 0-[3-phenyl-6-chloro-pyridazin-4-yl]S-(n-octyl)thiocarbonate is applied in an amount of 1 kg/ha, 0.2 kg/ha of Cyanazine is already sufficient to destroy all 3 weeds to a very good to excellent extent. If the amount of 0-[3-phenyl-6-chloro-pyridazin-4-yl]S-(n-octyl)thiocarbonate applied is increased to 1.5 kg/ha, 0.1 kg/ha of Cyanazine is already sufficient to cause a significant synergistic effect on, for example, *Anthemis arvensis*.

When combating weeds in cereal crops, it is therefore particularly advantageous to apply 0-[3-phenyl-6-chloropyridazin-4-yl]S-(n-octyl)thiocarbonate in an amount of 1 kg/ha and Cyanazine in an amount of 0.2 to 0.3 kg/ha.

The synergistic action of the composition according to the invention is illustrated in the following examples.

To calculate a synergistic effect, it was assumed that a purely additive effect can be calculated by the following equation:

$$E = X + Y - \frac{X \cdot Y}{100}$$

(from Limpel, L. E., P. H. Schuldt and D. Lamont, 1962, Weed control by dimethyl tetrachloroterephthalate alone and in certain combinations, Proc. NEWCC 16:48–53, based on Gowing, D. P. 1960, Comments on tests of herbicide mixtures, Weeds 8:379–391.)

E = (in the case of additive action) the degree of herbicidal action to be expected (% destruction of weeds) after using A + B in an amount of p + q kg/ha X = the degree of action (%) on using the active compound A in an amount of p kg/ha Y = the degree of action (%) on using the active compound B in an amount of q kg/ha.

If the value determined experimentally is higher than the value calculated according to the above formula, a synergistic effect exists, and if the value is lower, there is an antagonistic effect.

It can be clearly seen from the results in Tables 1 to 3 that in almost all cases, the degree of herbicidal action (% destruction) of a combination of the active compounds I + II is considerably greater than the values to be expected (calculated) in the case of a purely additive action.

The practical advantage of a synergistic effect as marked as that described here is exceptionally high. As is known, the E.W.R.C. rating scale for the degree of herbicidal action is based on an approximate exponential function between the degree of action (% destruction) and the particular figure of merit (or rating) such that the rating in the practical range between 85 and 100% destruction is considerably more precise than in the economically uninteresting range between 0 and 85% destruction (see Table 4).

It is considerably more important to increase the degree of action in the upper range than it is in the lower range. An improvement in the degree of action from, for example, 95% to 100% (+5%) is equivalent to an improvement by two figures of merit, whilst an increase in the degree of action from, for example, 70% to 80% (+10%) only corresponds to one step in the rating scale and moreover is of virtually no importance (both 70% and 80% destruction are still considered inadequate).

As can be seen from Example 4, however, increases in the synergistic action to an extent which is important economically can be detected in all cases, especially in the range between 85% and 100% destruction.

EXAMPLE 1

82 g of Cyanazine, 20 g of a Na dialkyl-sulfonate, 40 g of Na oleylmethyltauride, 48 g of champagne chalk and 410 g of highly disperse silica are initially introduced into a mixer and are mixed for 5 minutes. 400 g of Pyridate are then allowed to run in over a period of 20 minutes, whilst mixing intensively. After the addition, mixing is continued for a further 5–10 minutes and the mixture is then ground in a suitable mill. For use, the mixture thus obtained is suspended in water and sprayed onto the crops.

EXAMPLE 2

376 g of highly disperse silica are initially introduced into a mixer. 357 g of Pyridate are injected in over a period of 20 minutes, whilst mixing intensively, 147 g of Cyanazine, 50 g of Na lauryl-sulfate, 50 g of the Na salt of phenolsulfonic acid condensation products and 20 g of champagne chalk are added and mixing is carried out for 10 minutes. Finally, the formulation is ground in a suitable mill. For use, the mixture thus obtained is suspended in water and sprayed onto the crops.

EXAMPLE 3

334 g of Pyridate are sprayed onto 334 g of highly disperse silica in a mixer over a period of 15 to 20 minutes.

103 g of Cyanazine, 40 g of Na dodecylbenzenesulfonate, 30 g of Na lignin-sulfonate, 29 g of highly disperse silica and 130 g of champagne chalk are added to this 50% strength pre-concentrate, the components are mixed intimately and the mixture is then ground in a mill. For use, the mixture thus obtained is suspended in water and sprayed onto the crops.

Mixtures of Cyanazine and 0-[3-phenyl-6-chloro-pyridazin-4-yl]S-(n-propyl)thiocarbonate, 0-[3-phenyl-6-chloro-pyridazin-4-yl]S-(n-butyl)thiocarbonate, 0-[3-phenyl-6-bromo-pyridazin-4-yl]S-(n-butyl)thiocarbonate or 0-[3-phenyl-6-chloro-pyridazin-4-yl]S-(n-dodecyl)thiocarbonate can be formulated in an analogous manner.

EXAMPLE 4

The weeds *Anthemis arvensis* (corn chamomile), *Galium aparine* (catchweed bedstraw) and *Stellaria media* (chickweed) were sown, separated according to variety, in an experimental area in the open.

After the weeds had emerged and were in the stage of development in which they are usually combated with herbicides in cereal crops, they were sprayed in plots of 1 m² each with various amounts of the active compound components according to the invention. The compound 0-[3-phenyl-6-chloro-pyridazin-4-yl]S-(n-octyl)thiocarbonate was used in the following formulation:

50% by weight of the particular active substance
2% by weight of a Na alkylarylsulfonate
4% by weight of Na oleyl-methyltauride and
44% by weight of silica The compound 2-{[4-chloro-6-(ethylamino)-s-triazin-2-yl]amino}-2-methyl-propionitrile was used in the following formulation:
50% by weight of active substance
40% by weight of kaolin and
10% by weight of wetting agents and dispersing agents.

After 4 weeks, the weeds still remaining in the plots were harvested, again separated according to variety, and the green weight was determined. The amount of weed infestation in the untreated control plots was determined, by its weight, in the same manner. The residual weed infestation in the treated plots was compared to the weed infestation in the untreated plots and the particular degree of herbicidal action (% desctrucion) was thus found. In the case of the product mixture, these values were then investigated for any synergistic effects with the aid of the equation of Limpel et al.

TABLE 1

| | Degree of herbicidal action (% destruction) | | |
|---|---|---|---|
| | kg of active compound/ha | Anthemis arvensis (corn chamomile) found | Galium aparine (catchweed bedstraw) found | Stellaria media (chickweed) found |
| 0-(3-phenyl-6-chloro-pyridazin-4-yl) S-(n-octyl) thiocarbonate = I | 0.25 | 14 | 38 | 12 |
| | 0.50 | 44 | 66 | 60 |
| | 0.75 | 55 | 75 | 76 |
| | 1.00 | 70 | 91 | 82 |
| | 1.50 | 83 | 97 | 98 |
| 2-(4-chloro-6-ethylamino-s-triazin-2-yl-amino)-2-methyl-propionitrile = II | 0.10 | 20 | 43 | 10 |
| | 0.20 | 43 | 70 | 35 |
| | 0.30 | 60 | 76 | 63 |
| | 0.40 | 78 | 79 | 78 |

TABLE 2

| | | Degrees of herbicidal action (% destruction) | | | | | | | | |
|---|---|---|---|---|---|---|---|---|---|---|
| | | Anthemis arvensis | | | Galium aparine | | | Stellaria media | | |
| | kg of active compound/ha | found | calculated (E) | difference between found and calculated | found | calculated (E) | difference between found and calculated | found | calculated (E) | difference between found and calculated |
| I + II | 0.25 + 0.10 | 39 | 31 | +8 | 80 | 65 | +15 | 38 | 21 | +17 |
| | + 0.20 | 58 | 64 | −6 | 86 | 82 | +4 | 72 | 43 | +29 |
| | + 0.30 | 77 | 80 | −3 | 91 | 85 | +6 | 85 | 68 | +17 |
| | + 0.40 | 91 | 92 | −1 | 90 | 87 | +3 | 100 | 81 | +19 |
| I + II | 0.50 + 0.10 | 51 | 53 | −2 | 89 | 81 | +8 | 75 | 64 | +11 |
| | + 0.20 | 68 | 68 | 0 | 95 | 90 | +5 | 80 | 74 | +6 |
| | + 0.30 | 84 | 78 | +6 | 99 | 92 | +7 | 94 | 85 | +9 |
| | + 0.40 | 93 | 88 | +5 | 99 | 93 | +6 | 100 | 91 | +9 |
| I + II | 0.75 + 0.10 | 60 | 64 | −4 | 93 | 86 | +7 | 88 | 79 | +9 |
| | + 0.20 | 88 | 75 | +7 | 99 | 93 | +6 | 100 | 85 | +15 |
| | + 0.30 | 94 | 82 | +12 | 100 | 94 | +6 | 100 | 91 | +9 |
| | + 0.40 | 98 | 90 | +8 | 100 | 95 | +5 | 100 | 95 | +5 |

TABLE 3

| | | Degrees of herbicidal action (% destruction) | | | | | | | | |
|---|---|---|---|---|---|---|---|---|---|---|
| | | Anthemis arvensis | | | Galium aparine | | | Stellaria media | | |
| | kg of active compound/ha | found | calculated (E) | difference between found and calculated | found | calculated (E) | difference between found and calculated | found | calculated (E) | difference between found and calculated |
| I + II | 1.0 + 0.1 | 88 | 76 | +12 | 97 | 95 | +2 | 95 | 84 | +11 |
| | + 0.2 | 99 | 83 | +16 | 99 | 98 | +1 | 100 | 89 | +11 |
| | + 0.3 | 96 | 88 | +8 | 100 | 98 | +2 | 100 | 94 | +6 |
| | + 0.4 | 100 | 93 | +7 | 100 | 99 | +1 | 100 | 96 | +4 |

TABLE 3-continued

| | kg of active compound/ha | Anthemis arvensis | | | Galium aparine | | | Stellaria media | | |
|---|---|---|---|---|---|---|---|---|---|---|
| | | found | calculated (E) | difference between found and calculated | found | calculated (E) | difference between found and calculated | found | calculated (E) | difference between found and calculated |
| I + II | 1.5 + 0.1 | 96 | 86 | +10 | 100 | 98 | +2 | 100 | 99 | +1 |
| | + 0.2 | 96 | 90 | +6 | 100 | 99 | +1 | 100 | 100 | 0 |
| | + 0.3 | 100 | 93 | +7 | 100 | 99 | +1 | 100 | 100 | 0 |
| | + 0.4 | 100 | 96 | +4 | 100 | 99 | +1 | 100 | 100 | 0 |

TABLE 4

| | E.W.R.C. rating scale | |
|---|---|---|
| Figure of merit | Destruction of weeds | Effect produced by a formulation |
| 1 | 100% | excellent |
| 2 | 97.5% | very good |
| 3 | 95% | good |
| 4 | 90% | satisfactory |
| 5 | 85% | still adequate |
| 6 | 75% | inadequate |
| 7 | 65% | slight |
| 8 | 32.5% | very slight |
| 9 | 0 | none |

What we claim is:

1. A herbicidal post-emergence-composition consisting essentially of, as active ingredients, effective herbicidal amounts of 0-[3-phenyl-6-chloro-pyridazin-4-yl]-S-(n-octyl)-thiocarbonate and 2-{[4-chloro-6-(ethylamino)-s-triazin-2-yl]amino}-2-methylpropionitrile.

2. A herbicidal composition according to claim 1, wherein the weight ratio of the compound 2-{[4-chloro-6-(ethylamino)-s-triazin-2-yl]amino}-2-methylpropionitrile to the compound 0-[3-phenyl-6-chloro-pyridazin-4-yl]S-(n-octyl)thiocarbonate is in the range from 1:0.6 to 1:15.

3. A herbicidal composition according to claim 1, for use as wettable powder consisting of 12-45% by weight of the 0-[3-phenyl-6-chloro-pyridazin-4-yl]-S-(n-octyl)-thiocarbonate 3-20% by weight of 2-{[4-chloro-6-(ethylamino)-s-triazin-2-yl]amino}-2-methyl-propionitrile and 5-15% by weight of wetting and dispersing agents, made up to 100% by addition of inert fillers and carriers.

4. A process for combating weeds, comprising treating the crops after emergence of the plants, with a composition according to claim 1, the active compound 0-[3-phenyl-6-chloro-pyridazin-4-yl]-S-(n-octyl)thiocarbonate being applied in an amount of 0.25 to 1.5 kg/ha and the active compound 2-{[4-chloro-6-(ethylamino)-s-triazin-2-yl]amino}-2-methyl-propionitrile being applied in an amount of 0.1 to 0.4 kg/ha.

5. A process according to claim 4 for combating Anthemis arvensis, Stellaria media and Galium aparine virtually completely in cereal crops, comprising applying the active compound 0-[3-phenyl-6-chloro-pyridazin-4-yl]-S-(n-octyl)thiocarbonate; in an amount of 0.5 to 1.5 kg/ha and the active compound 2-{[4-chloro-6-(ethylamino)-s-triazin-2-yl]amino}-2-methyl-propionitrile in an amount of 0.1 to 0.4 kg/ha, whereby in cases where the active compound of 0-[3-phenyl-6-chloro-pyridazin-4-yl]-S-(n-octyl)thiocarbonate is applied in an amount of 0.5 to 0.75 kg/ha, the active compound 2-{[4-chloro-6-(ethylamino)-s-triazin-2-yl]amino}-2-methyl-propionitrile must be present in an amount of at least 0.3 kg/ha.

6. A process according to claim 5, wherein 0-[3-phenyl-6-chloro-pyridazin-4-yl]S-(n-octyl)thiocarbonate is used in an amount of 1 kg/ha and 2-{[4-chloro-6-(ethylamino)-s-triazin-2-yl]amino}-2-methyl-propionitrile is used in an amount of 0.2 to 0.3 kg/ha.

* * * * *